United States Patent [19]

Leise et al.

[11] Patent Number: 4,820,285

[45] Date of Patent: Apr. 11, 1989

[54] BAYONET COUPLING FOR OSTOMY DEVICE

[75] Inventors: Walter F. Leise, Yardley, Pa.; Kenneth A. Johnsen, Piscataway, N.J.

[73] Assignee: E.R. Squibb & Sons, Inc., Princeton, N.J.

[21] Appl. No.: 96,989

[22] Filed: Sep. 16, 1987

[51] Int. Cl.⁴ .................................................. A61F 5/44
[52] U.S. Cl. ....................................... 604/339; 285/376
[58] Field of Search ................................. 604/332–345; 215/222, 332, 341, 346; 285/331, 360, 361, 376, 396, 401, 402

[56] References Cited

U.S. PATENT DOCUMENTS

| 919,743 | 4/1909 | Mason | 285/361 |
| 3,736,934 | 6/1973 | Hennessy | 604/342 |
| 4,463,972 | 8/1984 | Weinhold | 285/331 |

FOREIGN PATENT DOCUMENTS

| 163979 | 9/1985 | European Pat. Off. |
| 1021145 | 3/1966 | United Kingdom |

Primary Examiner—John D. Yasko
Assistant Examiner—J. L. Kruter
Attorney, Agent, or Firm—Lawrence S. Levinson; Robert E. Lee, Jr.

[57] ABSTRACT

The bayonet coupling uses a body side flange and a bag side flange. The body side flange has L-shaped openings engaged to engage with pins on the body side flange. The body side flange includes an annular detent which includes an O-ring for sealing purposes.

3 Claims, 2 Drawing Sheets

BAYONET COUPLING FOR OSTOMY DEVICE

BACKGROUND OF THE INVENTION

The present invention relates to body waste receptacles and more particularly concerns a coupling device for use in connecting an ostomy bag to a wearer.

SUMMARY OF THE INVENTION

The bayonet flange system provides an easy to use means of couplng an ostomy bag and wafer. The unique feature of this invention is that the sealing and locking occur at different places. This allows coupling and uncoupling forces to remain very low, making it an ideal appliance to use post surgically to limit trauma at the surgical site. The flanges are coupled to one another by placing the arm of the bag side flange over the arm of the body side flange and twisting in a clockwise motion with a slight downward pressure. The body side pins will mate with the bag side slots and then move into the locked position. Because of its easy operation and reliable sealing and locking, this concept may also be used by ostomates on a regular basis.

DETAILED DESCRIPTION OF THE PREFERRED EMBODIMENT

Figure 1:
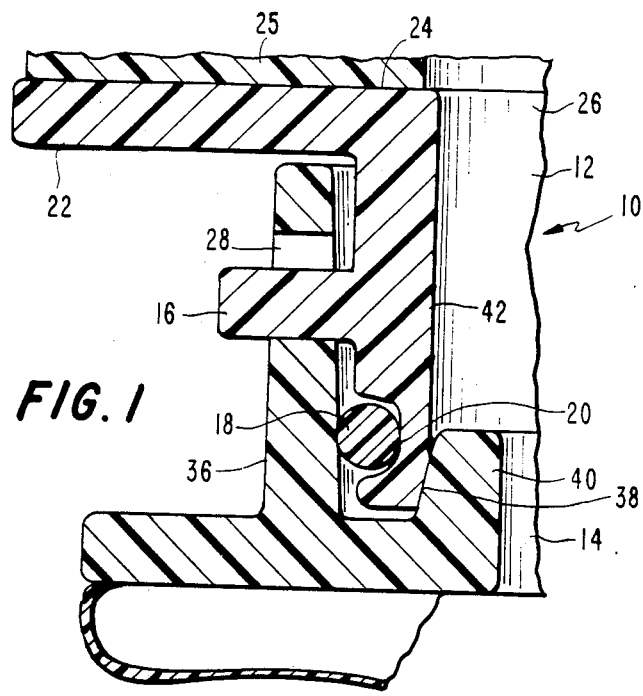
FIG. 1 is a cross-sectional view of the bayonet coupling system of the present invention.
Figure 2:
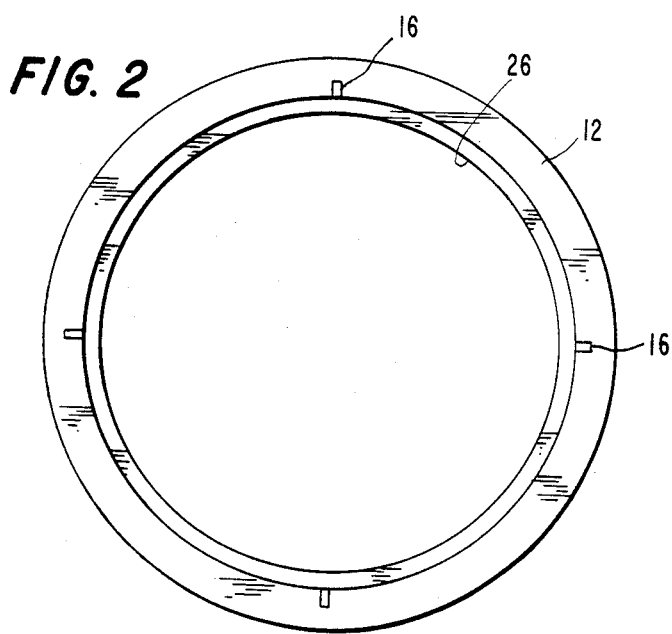
FIG. 2 is a bottom view of said body side coupling element.

Referring generally to FIG. 1, the bayonet flange system 10 of the present invention is comprised of a body side flange 12 and a bag side flange 14 designed to interlock with one another. The body side flange 12 has a plurality of locking pins 16 and a separate seal which is an O-ring seal 18 in the preferred embodiment of the invention 10. The O-ring seal 18 is held on the body side flange 12 by its internal tension and is located in an O-ring groove 20 formed within the body side flange 12. The body side flange 12 includes a leg 22 which provides a large flat surface 24 which may be used to bond the flange 12 to a wafer 25 of an adhesive, such as Stomahesive used to bond the flange 12 to a wearer's body. The body side flange 12 is substantially circular in shape and includes a central aperture 26 which surrounds a wearer's stomal opening when the invention 10 is in use.

Figure 3:
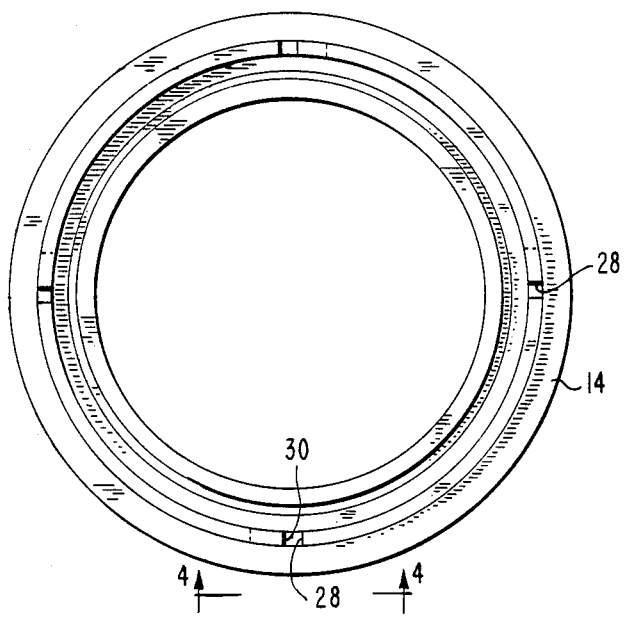
FIG. 3 is a top view of side bag side coupling element.
Figure 4:
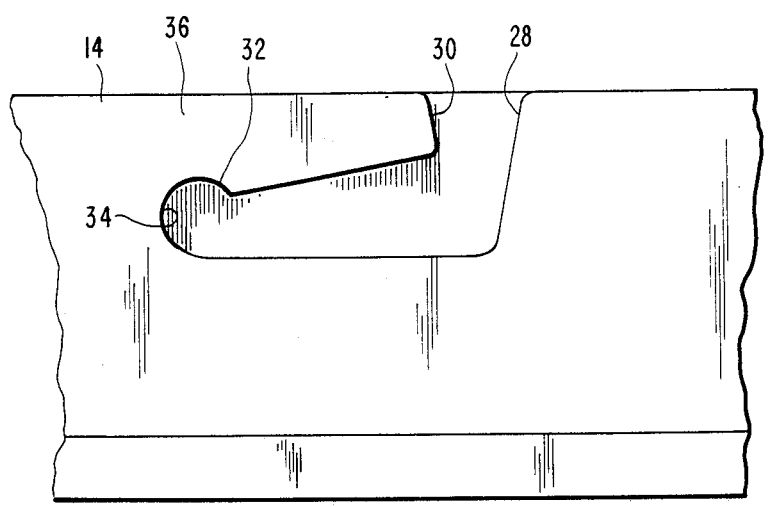
FIG. 4 is an enlarged side view of the bag side coupling element of FIG. 3 taken along the lines 44 in FIG. 3.

Referring to FIGS. 1, 3, and 4, bag side flange 14 has a plurality of tapered slots 28 having a wide entrance 30 to accept the pins 16 of the body side flange 12 and guide them to a locked position. A detent 32 adjacent to the terminal end 34 of the tapered slot 28 holds a pin 16 in the locked position. The arm 36 of the bag side flange 14 in which the tapered slots 28 are located is tapered axially on its inside surface 38 to allow easy assembly with the body side flange 12 and to guide the parts 12, 14 to an interlocking seal as they are pressed together. The inside diameter of the bag side flange 14 has a short tapered arm 40 to hold the arm 42 of the body side flange 12 and the O-ring 18 in contact with the large arm 36 of the bag side flange. This contact area 38 at the inside diameter of the flanges also prevents solids from entering the seal area adjacent to O-ring 18. The inside diameter of the body side flange 12 is straight and smooth to facilitate easy cleaning.

All parts used in this flange concept have been designed for manufacturing by standard molding processes.

We claim:

1. An improved coupling device for use in connecting an ostomy bag to a wearer of the type comprising a body side flange having a substantially circular shape with an aperture therein adapted to surround a stomal opening in a wearer and a flat surface thereon adapted to interface with an adhesive material for connecting said body side flange to said wearer, and a bag side flange adapted to be connected to said body side flange, said bag side flange holding a bag for receiving material which passes from said wearer, wherein the improvement comprises the combination of a bayonet coupling with an O-ring seal said bayonet coupling said body side flange to connect to said bag side flange without requiring significant pressure being applied against said body side flange and an O-ring seal adapted to seal said body side flange to said bag side flange, said body side flange comprising an annular arm at the periphery of said body said aperture and extending away from said flat surface, said body side arm having an annular detent therein wherein said O-ring seal is resiliently held, said body side flange further including a plurality of pins extending radially from said body side arm away from said aperture; said bag side flange comprising a first annular arm having a plurality of L-shaped openings for receiving said pins and a second annular arm spaced apart from said first annular arm to receive said body arm and press said O-ring therebetween.

2. The improved coupling device of claim 1 wherein said L-shaped opening on said bag side flange includes means for retaining said pins in a locked position.

3. The improved coupling device of claim 2 wherein said means for retaining said pins in the locked position are comprised of detents formed at the terminus of said L-shaped openings.

* * * * *